US007893279B2

(12) United States Patent
Ono et al.

(10) Patent No.: US 7,893,279 B2
(45) Date of Patent: Feb. 22, 2011

(54) CYCLOHEXANECARBOXYLIC ACID COMPOUND

(75) Inventors: Makoto Ono, Tokyo (JP); Shigeru Noguchi, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/574,907

(22) Filed: Oct. 7, 2009

(65) Prior Publication Data

US 2010/0022783 A1 Jan. 28, 2010

Related U.S. Application Data

(62) Division of application No. 10/562,122, filed as application No. PCT/JP2004/010457 on Jul. 23, 2004, now Pat. No. 7,691,894.

(30) Foreign Application Priority Data

Jul. 24, 2003 (JP) .............................. 2003-201062

(51) Int. Cl.
C07D 209/02 (2006.01)
(52) U.S. Cl. .................................................... 548/465
(58) Field of Classification Search ........................ None
See application file for complete search history.

(56) References Cited

U.S. PATENT DOCUMENTS

| 4,181,658 | A |   | 1/1980 | Hitzel et al. |     |
|-----------|---|---|--------|---------------|-----|
| 4,221,815 | A |   | 9/1980 | Weyer et al.  |     |
| 6,117,901 | A |   | 9/2000 | Wu et al.     |     |
| 7,691,894 | B2| * | 4/2010 | Ono et al.    | 514/414 |

FOREIGN PATENT DOCUMENTS

| DE | 25 00 157    | 7/1976  |
|----|--------------|---------|
| EP | 0 023 569    | 2/1981  |
| EP | 0 585 155    | 3/1994  |
| EP | 0 842 945    | 5/1998  |
| JP | 60 181081    | 9/1985  |
| JP | 04 112868    | 4/1992  |
| JP | 05 043574    | 2/1993  |
| JP | 2000 344666  | 12/2000 |
| WO | 95 30673     | 11/1995 |
| WO | 96 04267     | 2/1996  |
| WO | 96 22966     | 8/1996  |
| WO | 97 02024     | 1/1997  |
| WO | 97 03094     | 1/1997  |
| WO | 97 22619     | 6/1997  |
| WO | 98 04247     | 2/1998  |
| WO | 98 04913     | 2/1998  |
| WO | 98 08818     | 3/1998  |
| WO | 98 22430     | 5/1998  |
| WO | 99 33789     | 7/1999  |
| WO | 99/43672     | 9/1999  |
| WO | 99 61421     | 12/1999 |
| WO | 99 64392     | 12/1999 |
| WO | 00 00477     | 1/2000  |
| WO | 00 05223     | 2/2000  |
| WO | 00 05224     | 2/2000  |
| WO | 00 15612     | 3/2000  |
| WO | 00 18770     | 4/2000  |
| WO | 00 38223     | 6/2000  |
| WO | 00 40088     | 7/2000  |
| WO | 00 49005     | 8/2000  |
| WO | 00 61580     | 10/2000 |
| WO | 00 66119     | 11/2000 |
| WO | 00 68195     | 11/2000 |
| WO | 00 68213     | 11/2000 |
| WO | 01 00206     | 1/2001  |
| WO | 01 12186     | 2/2001  |
| WO | 01 34567     | 5/2001  |
| WO | 01 51487     | 7/2001  |
| WO | 01 53295     | 7/2001  |
| WO | 01 58871     | 8/2001  |
| WO | 01 64640     | 9/2001  |
| WO | 01 64659     | 9/2001  |
| WO | 02 04425     | 1/2002  |
| WO | 02 06222     | 1/2002  |
| WO | 02/53534     | 7/2002  |
| WO | 03 004460    | 1/2003  |

OTHER PUBLICATIONS

Chawla et al., "Challenges in Polymorphism of Pharmaceuticals", CRIPS vol. 5, No. 1, Jan.-Mar. 2004 (4 PAGES.*
Newman et al., "Solid-state analysis of the active pharmaceutical ingredient in drug products", DDT vol. 8, No. 19, Oct. 2003, p. 898-905.*
Multiple Scierosis, 19 pages.
www-marketwire-com (http://www.marketwire.com/mw/release.do?id=823166&sourceType=3), 2008.
www-redorbit-com (http://www.redorbit.com/modules/news/tools.php?tool=print&id=460088, 2005.
www-medicainewstoday-com (http:www.medicainewstoday.com/articles/75672.php), 2008.
Tilley et al. "VLA-4 antagonists", Drugs of the Future, vol. 26, No. 10, pp. 985-998 2001.

(Continued)

Primary Examiner—Sun Jae Y. Loewe
(74) Attorney, Agent, or Firm—Oblon, Spivak, McClelland, Maier & Neustadt, L.L.P.

(57) ABSTRACT

The present invention provides a VLA-4 inhibitor having high water-solubility and excellent long-term stability; i.e., sodium trans-4-[1-[2,5-dichloro-4-[(1-methyl-1H-3-indolylcarbonyl)amino]phenylacetyl]-(4S)-methoxy-(2S)-pyrrolidinylmethoxy]cyclohexanecarboxylate pentahydrate.

1 Claim, 3 Drawing Sheets

OTHER PUBLICATIONS

Yang et al. "VLA-4 Antagonists: Potent Inhibitors of Lymphocyte Migration", Medicinal Research Reviews, vol. 23, No. 3, pp. 369-392 2003.

Zimmerman. "Peptide and peptidomimetic inhibitors of VLA-4", Exp. Opin. Ther. Patents, vol. 9, No. 2, pp. 129-133 1999.

Duplantier et al. "Isoxazolyl, Oxazolyl, and Thiazolylpropionic Acid Derivatives as Potent alpha4beta1 Integrin Antagonists", Bioorganic and Medicinal Chemistry Letters, vol. 11, pp. 2593-2596 2001.

Kudlacz et al. "Pulmonary Eosinophilia in a Murine Model of Allergic Inflammation is Attenuated by Small Molecule alpha4beta1 Antagonists", Journal of Pharmacology and Experimental Therapeutics, vol. 301, No. 2, pp. 747-752 2002.

Palomer et al. "Derivation of Pharmacophore and CoMFA Models for Leukotriene D4 Receptor Antagonists of the Quinolinyl(bridged)aryl Series", J. Med. Chem., vol. 43, pp. 392-400 2000.

Scott et al. "High-Affinity Antagonists of the A4B1 Integrin", $220^{th}$ ACS National Meeting (Washington, DC)/MEDI.

Brittain et al., #2 "Effects of pharmaceutical processing on drug polymorphs and solvates" in Polymorphism in Pharmaceutical Solids, vol. 95, p. 331-361.

Express-Pharma-Online (http://www.expresspharmaonline.com/20031023/edit02.shtml).

\* cited by examiner

A (Type-I)

B (Type-II)

CYCLOHEXANECARBOXYLIC ACID COMPOUND

CROSS-REFERENCE TO RELATED APPLICATIONS

This application is a divisional of U.S. Ser. No. 10/562,122 filed Dec. 23, 2005, now U.S. Pat. No. 7,691,894, which was a 371 of PCT/JP04/10457 filed Jul. 23, 2004 and claims the benefit of JP 2003-201062 filed Jul. 24, 2003.

TECHNICAL FIELD

The present invention relates to a cyclohexanecarboxylic acid compound which is excellent in VLA-4 (very late antigen-4) inhibitory action, water-solubility and long-term storage stability, thus is useful as a preventive and/or therapeutic drug for disorders caused by cell adhesion. This invention also relates to a medicine containing the compound.

BACKGROUND ART

It is known that certain diseases can be prevented and treated by inhibition of cell adhesion as such pathological relationship comes to be increasingly clear. Some cell adhesion molecules are involved in cell adhesion, and VLA-4 is known as a molecule having a role in mediating adhesion of leukocytes. On the basis of this knowledge, a variety of VLA-4 inhibitors have been developed. Patent document 1 discloses a compound which exhibits excellent VLA-4 inhibitory activity and thus is useful as a preventive and/or therapeutic drug for disorders caused by cell adhesion.

Example 170 of Patent document 1 discloses that trans-4-[1-[2,5-dichloro-4-[(1-methyl-1H-3-indolylcarbonyl)amino]phenylacetyl]-(4S)-methoxy-(2S)-pyrrolidinylmethoxy]cyclohexanecarboxylic acid (hereinafter referred to as compound (a)) was isolated as a colorless solid.

[Chemical formula 1]

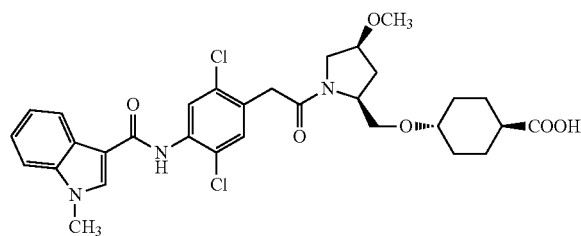

(a)

[Patent document 1] WO 02/053534

DETAILED DESCRIPTION OF THE INVENTION

Problem to be Solved by the Invention

However, compound (a), isolated as a colorless solid in Patent document 1, has low water-solubility, and a concern about long-term stability. Water-solubility and long-term storage stability are crucial factors to be considered in developing a drug product from compound (a).

Means for Solving the Problem

In view of the foregoing, the present inventors performed extensive studies to obtain a compound which not only exerts pharmacological effects, but also has excellent water-solubility and long-term storage stability and thus is useful as a medicinal drug. In the end, it was found that a sodium salt pentahydrate of compound (a) described above could bring about higher water-solubility as compared with other salts of compound (a), was free from any problem regarding moisture adsorption/desorption while keeping long-term storage stability, therefore being a useful component of a medicinal product. Thus the present invention was achieved.

Accordingly, the present invention provides sodium trans-4-[1-[2,5-dichloro-4-[(1-methyl-1H-3-indolylcarbonyl)amino]phenylacetyl]-(4S)-methoxy-(2S)-pyrrolidinylmethoxy]cyclohexanecarboxylate pentahydrate (hereinafter referred to as "compound (1)") represented by the following formula (1):

[Chemical formula 2]

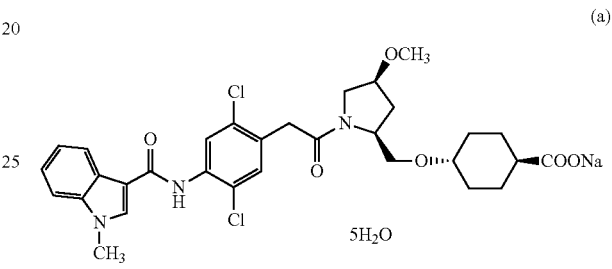

(a)

The present invention also provides crystals of compound (1).

The present invention also provides a medicine containing compound (1) as an active ingredient.

The present invention also provides a medicinal composition containing compound (1) and a pharmaceutically acceptable carrier therefor.

The present invention further provides use of compound (1) for the manufacture of a medicine.

The present invention still further provides a method for treating disorders caused by cell adhesion, characterized by administering a compound (1) in an effective dose.

Advantageous Effect of the Invention

The compound (1) of the present invention has high water-solubility. The weight of compound (1) changes a little by water adsorption/desorption, and thus compound (1) has excellent storage stability. The compound (1) also has excellent VLA-4 inhibitory activity. Therefore, the compound (1) of the present invention is useful as a preventive and/or therapeutic drug for disorders caused by cell adhesion.

BEST MODE FOR CARRYING OUT THE INVENTION

Figure 1:
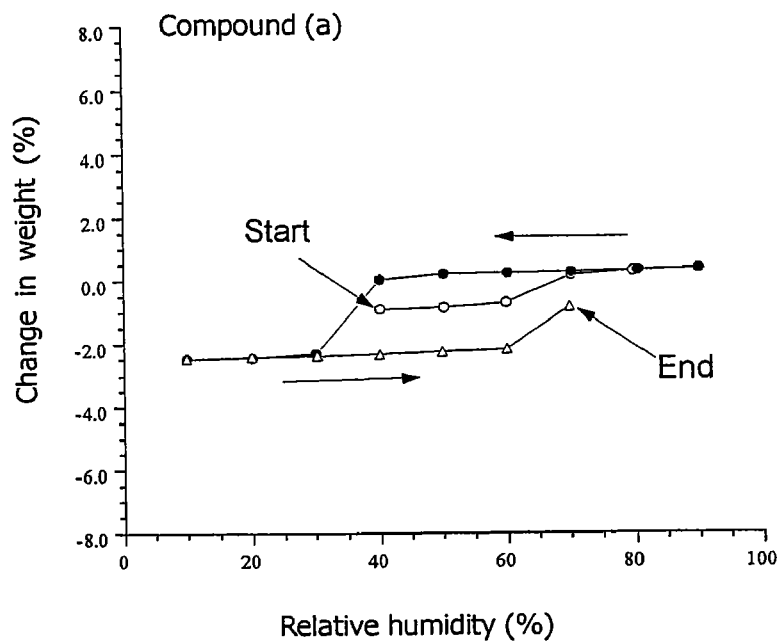
FIG. 1 shows moisture adsorption/desorption behavior of compound (a).

Compound (1) is a sodium salt pentahydrate of compound (a) disclosed in Patent document 1. Therefore, compound (1) can be produced through reaction of compound (a) or a mixture containing compound (a) with a compound capable of providing sodium ions and crystallization of the reaction product from a hydrated solvent. Examples of the compound capable of providing sodium ions include sodium salts such as sodium hydroxide and sodium carbonate, with sodium hydroxide being particularly preferred. The reaction of compound (a) with the sodium-ion-providing compound may be carried out at 20 to 35° C. through addition of an aqueous solution of 1.0 to 1.2 mol of the sodium-ion-providing compound on the basis of compound (a).

After compound (a) has been completely dissolved in the mixture, insoluble matter is removed therefrom in need, and compound (1) is crystallized from a hydrated solvent. Examples of the hydrated solvent employed in the present invention include hydrated acetone, hydrated acetonitrile, hydrated 1-propanol, hydrated 2-propanol, and hydrated ethanol. Hydrated acetone is particularly preferred.

The thus-produced compound (1) was found to have high water-solubility as compared with compound (a) and other salts such as an ethanolamine salt, a dibenzylethylenediamine salt, and a lithium salt of compound (a), as is shown in the Examples described below.

Moisture adsorption/desorption of different salts of compound (a) were studied, and long-term storage stability of each salt was determined from the results. Compound (a) exhibited a weight change, so that it was impossible to determine its hydrated form. Compound (1) and a lithium salt, an ethanolamine salt, a dibenzylethylenediamine salt of compound (a) exhibited no weight change under typical humidity conditions and were stable. A t-butylamine salt of compound (a) exhibited a slight weight change.

Among these compounds, only compound (1) was found to exhibit both good water-solubility and good moisture adsorption/desorption characteristics (storage stability).

During the crystallization of compound (1), crystal polymorphism is induced by a stirring stimulation. When such a stirring stimulation is weak, plate-like crystals (Type-II) are produced, whereas when that is strong, needles (Type-I) are produced. Type-II crystals exhibit characteristic peaks of angle of diffraction (2θ) at 7.2, 17.3, 18.9, 19.4, 20.4, and 21.6 (°) as measured through powder x-ray diffractometry. On the other hand, type-I crystals exhibit characteristic peaks of angle of diffraction (2θ) at 7.2, 12.9, 17.3, 18.9, 19.8, 21.6, 26.8, and 30.5 (°) as measured through powder x-ray diffractometry.

Both of Type-I and Type-II crystals of compound (1) were found to have high water-solubility and good storage stability (moisture adsorption/desorption property). However, from the viewpoints of control of crystallization conditions and handling in mass production, Type-II crystals are preferred.

As described above, compound (1) of the present invention has high water-solubility and good storage stability. As described in Patent Document 1, compound (1) of the present invention can selectively inhibit binding of cell adhesion molecules with VLA-4. Therefore, compound (1) of the present invention is useful as a preventive and/or therapeutic drug for disorders caused by cell adhesion involving VLA-4; i.e., mediated by migration and adhesion of leukocytes. Examples of such disorders include inflammatory diseases, autoimmune diseases, cancerous metastasis, bronchial asthma, nasal obstruction, diabetes, arthritis, psoriasis, multiple sclerosis, inflammatory bowel disease, and transplantation rejection.

The medicine of the present invention may be administered through oral administration or other administration routes. When the medicine of the invention is used as an injection, the medicine may be administered through any route such as intravenous injection, intramuscular injection, or subcutaneous injection.

The dosage form of the medicine may be determined depending on adopted administration routes, and the preparation may be produced through a conventional method. Examples of the dosage form for a oral drug include tablets, powders, granules, capsules, solutions, syrups, elixirs, and oil-base or water-base suspensions. A preparation for injection may contain, for example, a stabilizer, a preservative, or a solubilizer. A solution which may contain any of these auxiliary agents may be contained in a container, and, if desired, may be subjected to lyophilization or a similar process, to thereby produce a solid product, which may be returned to solution upon use. Examples of liquid formulations include solutions, suspensions, and milky lotions. When any of these liquid drugs is produced, additives such as suspending agents and emulsifiers may be used.

A medicine containing compound (1) of the present invention is preferably administered to adult by repeating once/day administration at suitable intervals. The daily dose of compound (1) is 0.01 mg to 2,000 mg, preferably 0.1 mg to 1,000 mg.

The medicine of the present invention may be used, if necessary, in combination with an anti-inflammatory agent, an anti-arthritic drug, adrenocorticosteroid (corticosteroid), an immunosuppressant, an antipsoriatic drug, a bronchodilator, an anti-bronchial asthma drug, or an antidiabetic drug, so long as the effect of the medicine of the present invention is not impaired.

EXAMPLES

The present invention will next be described in more detail by way of examples.

Referential Example 1 (Synthesis of compound (a))

Methyl trans-4-[(4S)-methoxy-(2S)-pyrrolidinylmethoxy]cyclohexanecarboxylate (100 mg, 0.37 mmol) was dissolved in DMF (2 mL). To the solution, [2,5-dichloro-4-[(1-methyl-1H-3-indolylcarbonyl)amino]phenyl]acetic acid (140 mg, 0.37 mmol), 1-hydroxybenzotriazole (HOBt) (95 mg, 0.70 mmol), dimethylaminopyridine (DMAP) (catalytic amount), and 1-ethyl-3-(3-dimethylaminopropyl)carbodiimide hydrochloride (EDC.HCl) (107 mg, 0.56 mmol) were added. The mixture was stirred for 18 hours at room temperature. The reaction mixture was poured to 1M-HCl, followed by extraction with ethyl acetate three times. The resultant extract was washed with saturated brine and then dried over magnesium sulfate anhydrate, and the solvent was removed under reduced pressure. The residue was purified through silica gel column chromatography (middle pressure Yamazen, chloroform/methanol 10:0 to 97:3, 20 mL/min, φ50 mm×150 mm). The thus-obtained ester was dissolved in THF (4 mL), and 0.25M NaOH (2.4 mL, 0.61 mmol) was added thereto. The mixture was stirred for 18 hours at room temperature, and the solvent was removed under reduced pressure. The residue was crystallized through addition of 1M HCl. The precipitated crystals were collected through filtration under reduced pressure, washed with water, and then dried under reduced pressure, to thereby yield a compound (a) (150 mg, 66%) as a colorless solid.

$^1$H-NMR (DMSO-d$_6$) δ: 1.10-1.40 (m, 4H), 1.80-2.20 (m, 8H), 3.15-4.30 (m, 8H), 3.28 (s, 3H), 3.90 (s, 3H), 7.21 (t, J=7.5 Hz, 1H), 7.28 (t, J=7.5 Hz, 1H), 7.50 (d, J=15.2 Hz, 1H), 7.56 (d, J=8.3 Hz, 1H), 7.88 (d, J=4.1 Hz, 1H), 8.15 (d, J=8.0 Hz, 1H), 8.31 (s, 1H), 9.39 (s, 1H).

MS (ESI) m/z 617 (M+1)$^+$;

Anal. Calcd for C$_{31}$H$_{35}$Cl$_2$N$_3$O$_6$.0.5H$_2$O: C, 59.52; H, 5.80; N, 6.72.

Found: C, 59.36; H, 5.72; N, 6.68.

Example 1

Synthesis of Compound (1): Type-I

The compound (a) (5.0 g, 8.1 mol) was suspended in acetone (100 mL), and 1M aqueous NaOH (8.1 mL) was added to the suspension, followed by stirring for 18 hours at room temperature by use of a stirrer. The precipitated crystals were collected through filtration under reduced pressure, washed with acetone, and then dried under reduced pressure. Moisture conditions of the thus-dried crystals were controlled in an atmosphere having a relative humidity of 52% or higher, to thereby yield 5.6 g (95%) of the title compound (1) as white needles. The compound was identified to be of Type-I through powder x-ray diffractometry.

Anal. Calcd. For C$_{31}$H$_{34}$Cl$_2$N$_3$NaO$_6$.5H$_2$O: C, 51.10; H, 6.09; N, 5.76; Cl, 9.73; Na, 3.16.

Found: C, 50.80; H, 5.99; N, 5.60; Cl, 9.70; Na, 3.41.

Example 2

Synthesis of Compound (1): Type-II

The compound (1) (15.0 g) was dissolved in 50% hydrated acetone (90 mL) at 30 to 40° C. Insoluble matter was removed through filtration, and acetone (360 mL) was added to the filtrate, followed by stirring for 20 hours at room temperature by use of stirring blades. The precipitated crystals were collected through filtration under reduced pressure, washed with 10% hydrated acetone, and then dried under reduced pressure. Moisture conditions of the thus-dried crystals were controlled in an atmosphere of a relative humidity of 52% or higher, to thereby yield 14.2 g (95%) of the title compound (1) as white plate-like crystals. The thus-obtained compound was identified to be of Type-II through powder x-ray diffractometry.

Comparative Example 1 (Synthesis of a lithium salt of compound (a))

The compound (a) (112 mg, 0.18 mmol) was suspended in ethanol (5 mL), and 1M aqueous LiOH (0.18 mL) was added to the suspension. The solvent was removed under reduced pressure, whereby the mixture was dried to solid. The residue was dissolved in 20% hydrated acetonitrile (3 mL) with heat, and the solution was allowed to stand for two days at 4° C. The thus-precipitated crystals were collected through filtration under reduced pressure and then dried at room temperature for one day, to thereby yield 98 mg (78%) of a lithium salt of compound (a) as white crystals.

Anal. Calcd. For C$_{31}$H$_{34}$Cl$_2$LiN$_3$O$_6$.4H$_2$O: C, 53.61; H, 6.10; N, 6.05; Cl, 10.21.

Found: C, 53.47; H, 6.08; N, 6.02; Cl, 10.33.

Similarly, an ethanolamine salt, a dibenzylethylenediamine salt, and a t-butylamine salt of compound (a) were prepared.

Test Example 1

Compound (1), compound (a), and salts of compound (a) prepared in Example 1, Referential Example 1, and Comparative Example 1, respectively, were evaluated in terms of moisture adsorption/desorption. Specifically, the amount of water adsorbed on or desorbed from each compound was determined through subjecting crystals (about 20 mg) of each compound to a microbalance (automatic vapor adsorption apparatus) and measuring time-elapsed change in weight at relative humidities (RH) ranging from 10 to 90%.

Figure 2:
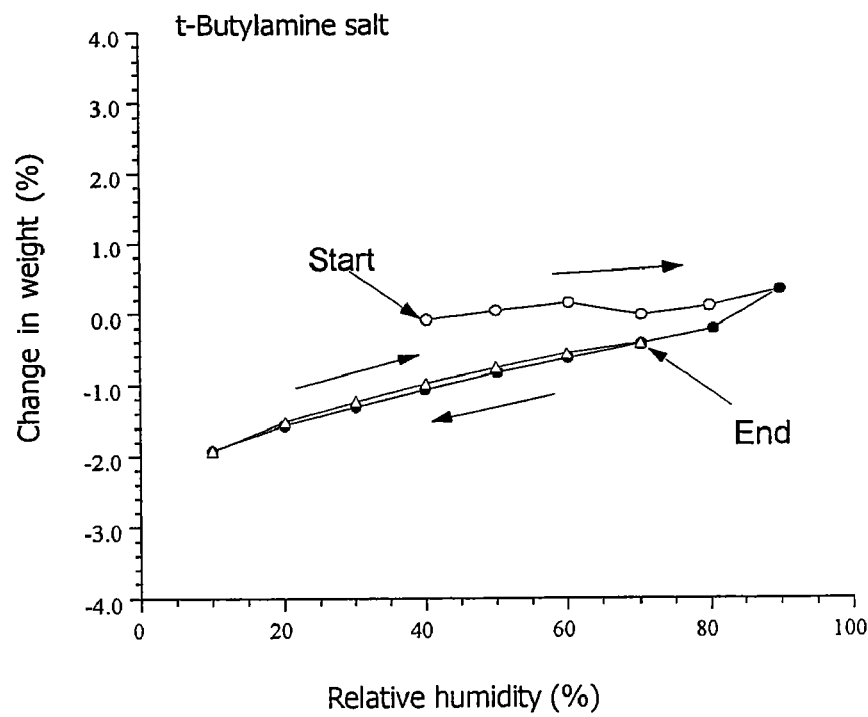
FIG. 2 shows moisture adsorption/desorption behavior of a t-butylamine salt of compound (a).
Figure 3:
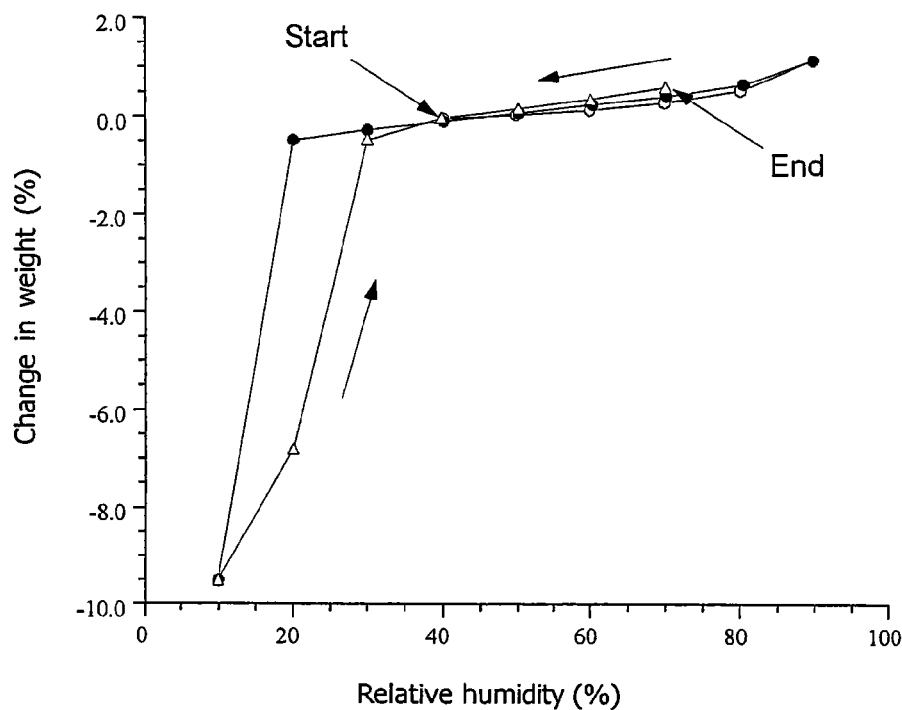
FIG. 3 shows moisture adsorption/desorption behavior of compound (1).

As a result, compound (a) was found to exhibit a change in weight at 40 to 60% RH, and its hydrated form was difficult to determine (FIG. 1). The t-butylamine salt of compound (a) was found to exhibit a slight change in weight, indicating that the salt raises a concern regarding storage stability (FIG. 2). In contrast, compound (1) was found to exhibit no change in weight under typical humidity conditions and thus be stable (FIG. 3). The lithium salt, ethanolamine salt, and dibenzylethylenediamine salt of compound (a) were found to be stable under typical humidity conditions.

Test Example 2

Compound (1), compound (a), and salts of compound (a) prepared in Example 1, Referential Example 1, and Comparative Example 1, respectively were evaluated in terms of solubility to water (37° C.).

As a result, as shown in Table 1, compound (a) was found to have considerably low water-solubility. In contrast, compound (1) and the t-butylamine salt of compound (a) were found to have very high water-solubility.

TABLE 1

|  | Water Solubility (μg/mL) |
| --- | --- |
| Compound (a) | 0.653 |
| Ethanolamine salt | 896 |
| Dibenzylethylenediamine salt | 74.3 |
| Lithium salt | 838 |
| t-Butylamine salt | >1000 |
| Compound (1) | >1000 |

Example 3

Examples 1 and 2 shows that the forms of produced crystals varies depending on crystallization conditions. Attempts were made to control crystal polymorphism. The results indicate that the crystal form cannot be controlled by crystallization temperature, water content of the hydrated solvent, or stirring time, but can be controlled by a stirring stimulation. Specifically, when such a stirring stimulation is week (stirring with blades), Type-II crystals (plate-like crystals) were produced, whereas when that is strong (stirring with stirrer), Type-I crystals (needles) were produced.

We studied crystal transition over time at stirring with blades in 10% hydrated-acetone. As a result of powder x-ray diffractory of generated crystals, the diffraction patterns show that a peak at 2θ=20° attributed to Type-I crystals appeared three days after starting of stirring, and the peak grew as the stirring time extended. These results suggest that crystal transition to Type-I occurs under stirring with blades at room temperature.

Figure 4:
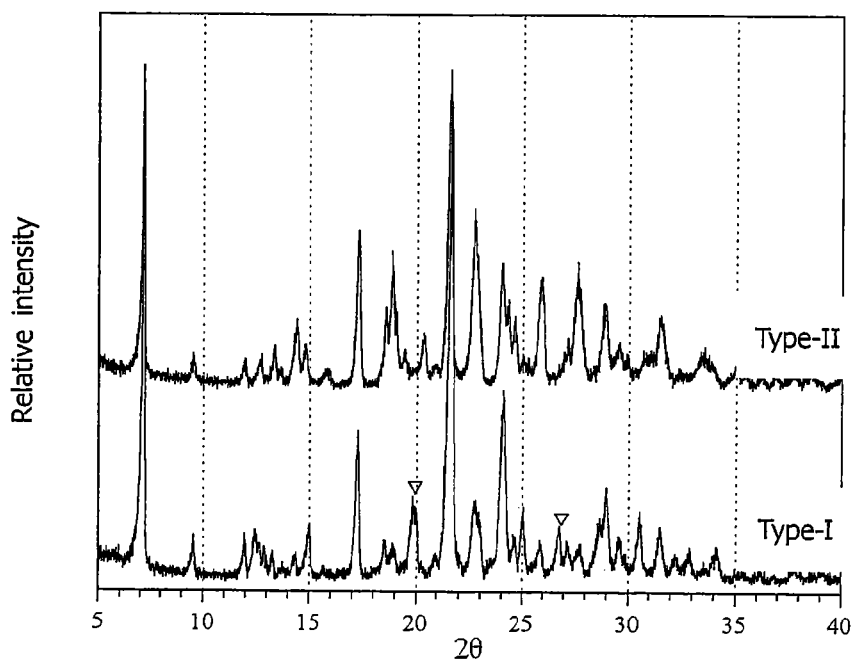
FIG. 4 shows powder x-ray diffractometry spectra of Type-I crystals and Type-II crystals of compound (1).

FIG. 4 shows powder x-ray diffraction patterns of Type-I and Type-II crystals, and Table 2 shows peaks of the patterns.

TABLE 2

| Type-I crystals | | Type-II crystals | |
|---|---|---|---|
| Angle of diffraction 2θ (°) | Intensity | Angle of diffraction 2θ (°) | Intensity |
| 7.2 | Intense | 7.2 | Intense |
| 9.6 | Weak | 9.5 | Weak |
| 12.0 | Weak | 11.9 | Weak |
| 12.5 | Weak | 12.7 | Weak |
| 12.9 | Weak | 13.4 | Weak |
| 13.3 | Weak | 14.4 | Medium |
| 14.4 | Weak | 14.8 | Weak |
| 15.0 | Medium | 15.8 | Weak |
| 17.3 | Slightly intense | 17.3 | Slightly intense |
| 18.5 | Weak | 18.6 | Medium |
| 18.9 | Weak | 18.9 | Slightly intense |
| 19.8 | Medium | 19.4 | Weak |
| 21.6 | Intense | 20.4 | Weak |
| 22.7 | Medium | 21.6 | Intense |
| 24.1 | Slightly intense | 22.7 | Slightly intense |
| 24.6 | Weak | 24.0 | Medium |
| 25.1 | Medium | 24.3 | Medium |
| 25.8 | Weak | 24.6 | Medium |
| 26.8 | Medium | 25.0 | Weak |
| 27.1 | Weak | 25.9 | Medium |
| 27.7 | Weak | 27.6 | Medium |
| 29.0 | Medium | 28.9 | Medium |
| 29.6 | Weak | 29.6 | Weak |
| 30.5 | Medium | 31.5 | Medium |
| 31.5 | Medium | 33.6 | Weak |
| 32.2 | Weak | 35.0 | Weak |

TABLE 2-continued

| Type-I crystals | | Type-II crystals | |
|---|---|---|---|
| Angle of diffraction 2θ (°) | Intensity | Angle of diffraction 2θ (°) | Intensity |
| 32.9 | Weak | 35.5 | Weak |
| 34.1 | Weak | | |

Figure 5:
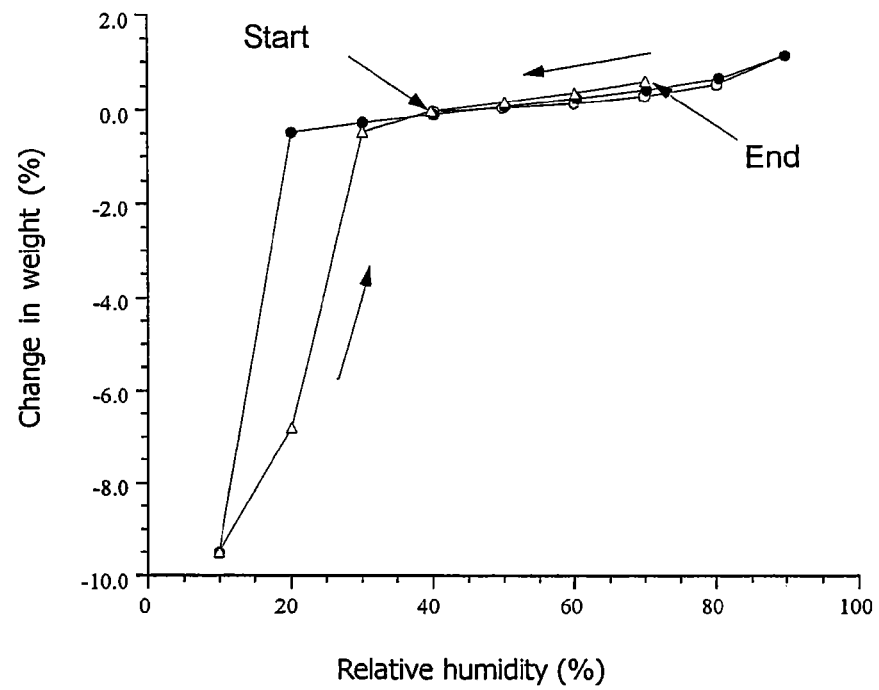
FIG. 5 shows moisture adsorption/desorption behavior of Type-I crystals (A) and Type-II crystals (B) of compound (1).
Figure 5:
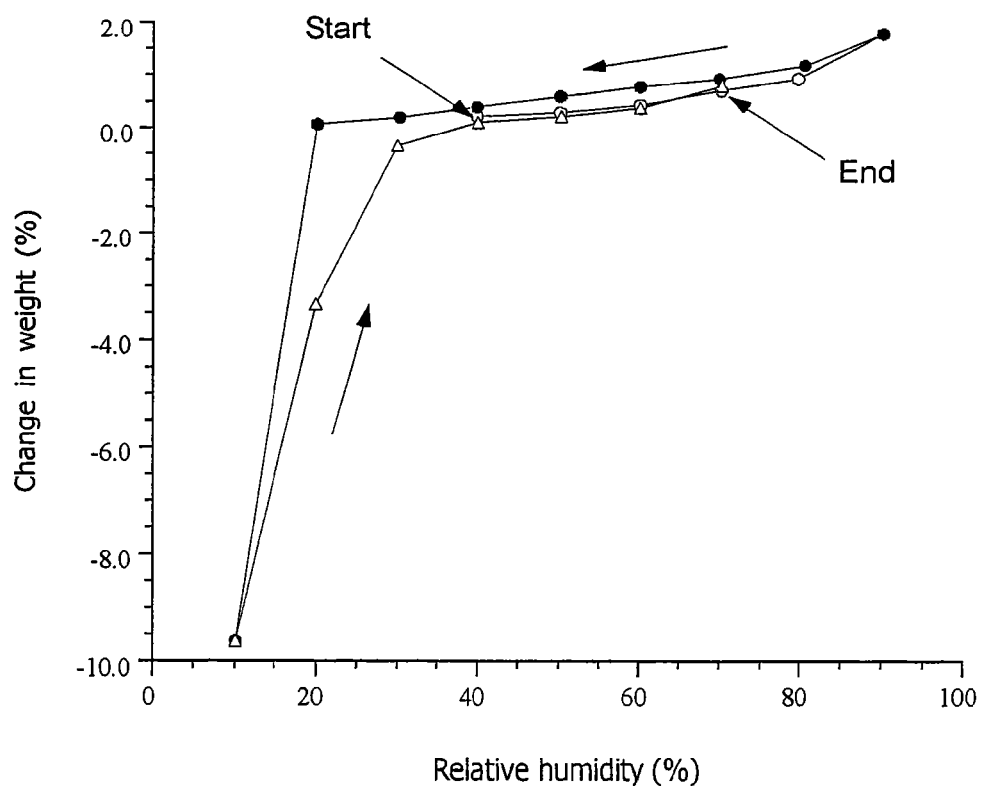

Type-I and Type-II crystals were evaluated in terms of moisture adsorption/desorption and water-solubility in a manner similar to that described in Test Examples 1 and 2. The results are shown in FIG. 5 and Table 3.

TABLE 3

| Crystal form | Water Solubility (μg/mL) |
|---|---|
| Type-I | >1000 |
| Type-II | >1000 |

The compound (1) of the present invention was found to have a VLA-4 inhibitory activity comparable to that of compound (a).

The invention claimed is:

1. Sodium trans-4-[1-[2,5-dichloro-4-[(1-methyl-1H-3-indolylcarbonyl)amino]phenylacetyl]-(4S)-methoxy(2S)-pyrrolidinylmethoxy]cyclohexanecarboxylate pentahydrate, which is in the form of Type I crystals having the full XRD pattern of FIG. 4.

* * * * *